(12) United States Patent
Wabel et al.

(10) Patent No.: US 11,964,085 B2
(45) Date of Patent: Apr. 23, 2024

(54) APPARATUS AND METHOD FOR FILLING SOLUTION BAGS FOR DIALYSIS

(71) Applicant: Fresenius Medical Care Deutschland GmbH, Bad Homburg (DE)

(72) Inventors: Peter Wabel, Rosbach (DE); Marcus Breuninger, Bad Homburg (DE); Robert Berlich, St. Wendel (DE); Birgit Staude, Pfungstadt (DE); Matthias Rau, Wiesbaden (DE); Zdenek Cerman, Idstein (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 859 days.

(21) Appl. No.: 16/971,414

(22) PCT Filed: Feb. 14, 2019

(86) PCT No.: PCT/EP2019/053661
§ 371 (c)(1),
(2) Date: Aug. 20, 2020

(87) PCT Pub. No.: WO2019/162181
PCT Pub. Date: Aug. 29, 2019

(65) Prior Publication Data
US 2021/0001029 A1    Jan. 7, 2021

(30) Foreign Application Priority Data

Feb. 21, 2018   (DE) .......................... 102018103863.1

(51) Int. Cl.
*A61M 1/16*   (2006.01)
*B65B 3/00*   (2006.01)

(52) U.S. Cl.
CPC ........ *A61M 1/1668* (2014.02); *A61M 1/1686* (2013.01); *B65B 3/003* (2013.01); *A61M 2209/045* (2013.01)

(58) Field of Classification Search
None
See application file for complete search history.

(56) References Cited

U.S. PATENT DOCUMENTS

| | | |
|---|---|---|
| 4,905,450 A | 3/1990 | Hansen et al. |
| 2002/0023409 A1 | 2/2002 | Py |

(Continued)

FOREIGN PATENT DOCUMENTS

| | | |
|---|---|---|
| CN | 102145774 | 8/2011 |
| CN | 105079901 | 11/2015 |

(Continued)

*Primary Examiner* — Krishnan S Menon
(74) *Attorney, Agent, or Firm* — Jacobson Holman PLLC

(57) ABSTRACT

The present invention relates to an apparatus and to a method for filling a solution bag for dialysis with a liquid, wherein the apparatus comprises a needle for introduction into a filling line or filling opening of the bag, wherein the needle is a double wall needle having a preferably thermally conductive outer wall and having an inner wall, with a thermal insulation being present between the outer wall and the inner wall; and with a heating element being provided that is configured to heat the outer side of the outer wall to a temperature above the temperature of the inner side of the inner wall.

12 Claims, 3 Drawing Sheets

(56) References Cited

U.S. PATENT DOCUMENTS

Figure 1:
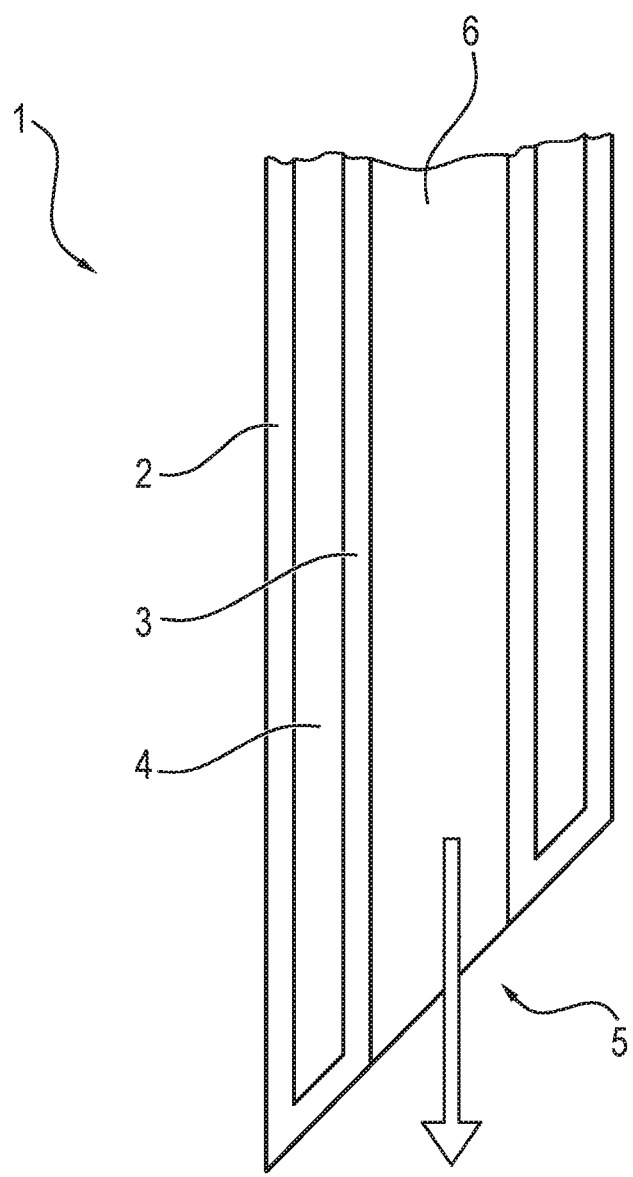

| | | | |
|---|---|---|---|
| 2002/0124526 A1 | 9/2002 | Lewis, Jr. et al. | |
| 2004/0256026 A1* | 12/2004 | Py | B29C 65/18 |
| | | | 141/329 |
| 2006/0191594 A1 | 8/2006 | Py | |
| 2008/0281292 A1* | 11/2008 | Hickingbotham | A61M 5/14244 |
| | | | 604/521 |
| 2014/0276427 A1* | 9/2014 | Chi | A61M 5/148 |
| | | | 604/151 |
| 2019/0329018 A1* | 10/2019 | Glaser | A61M 39/12 |

FOREIGN PATENT DOCUMENTS

| | | |
|---|---|---|
| CN | 106413784 | 2/2017 |
| GB | 831922 | 4/1960 |
| WO | WO2017/127632 | 7/2017 |

* cited by examiner

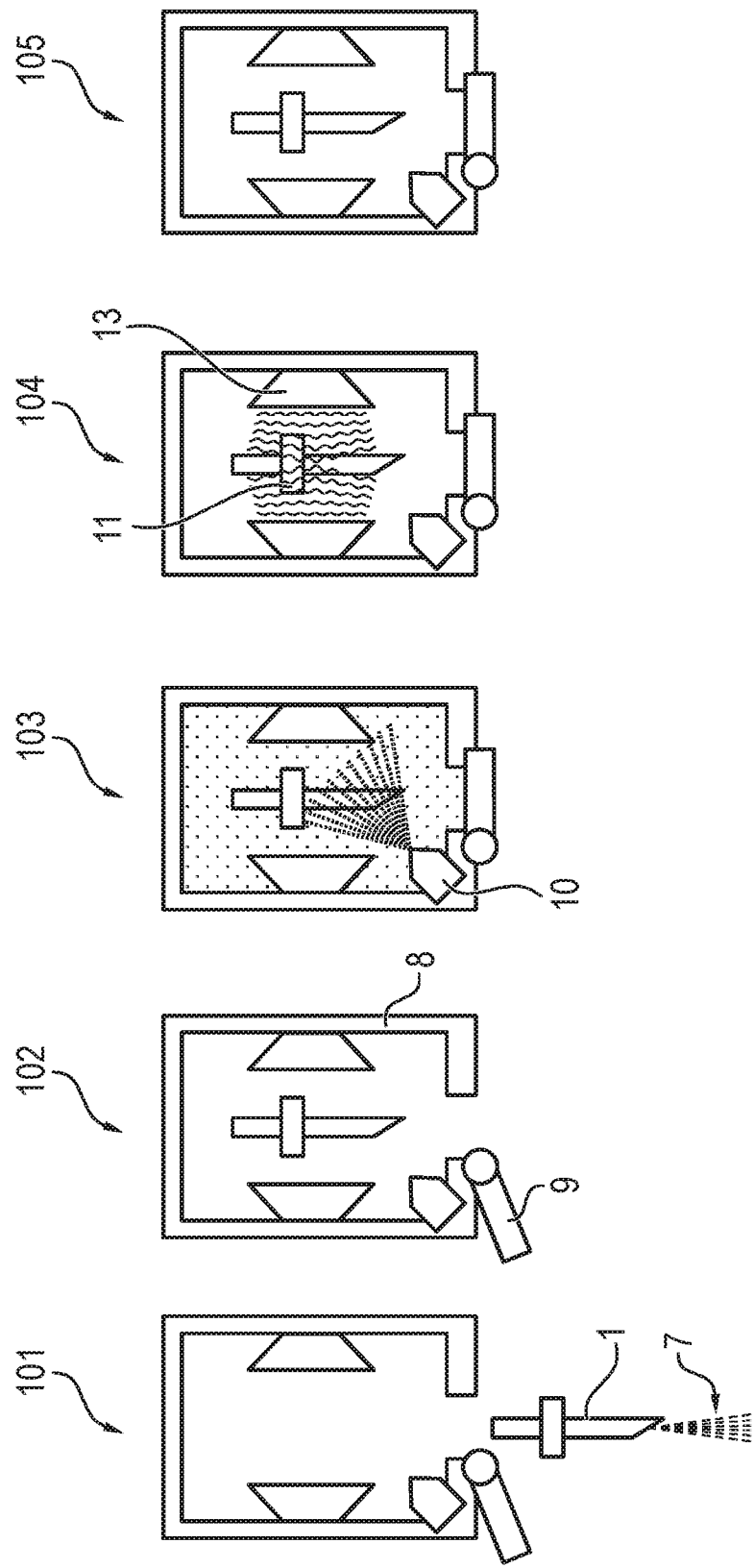

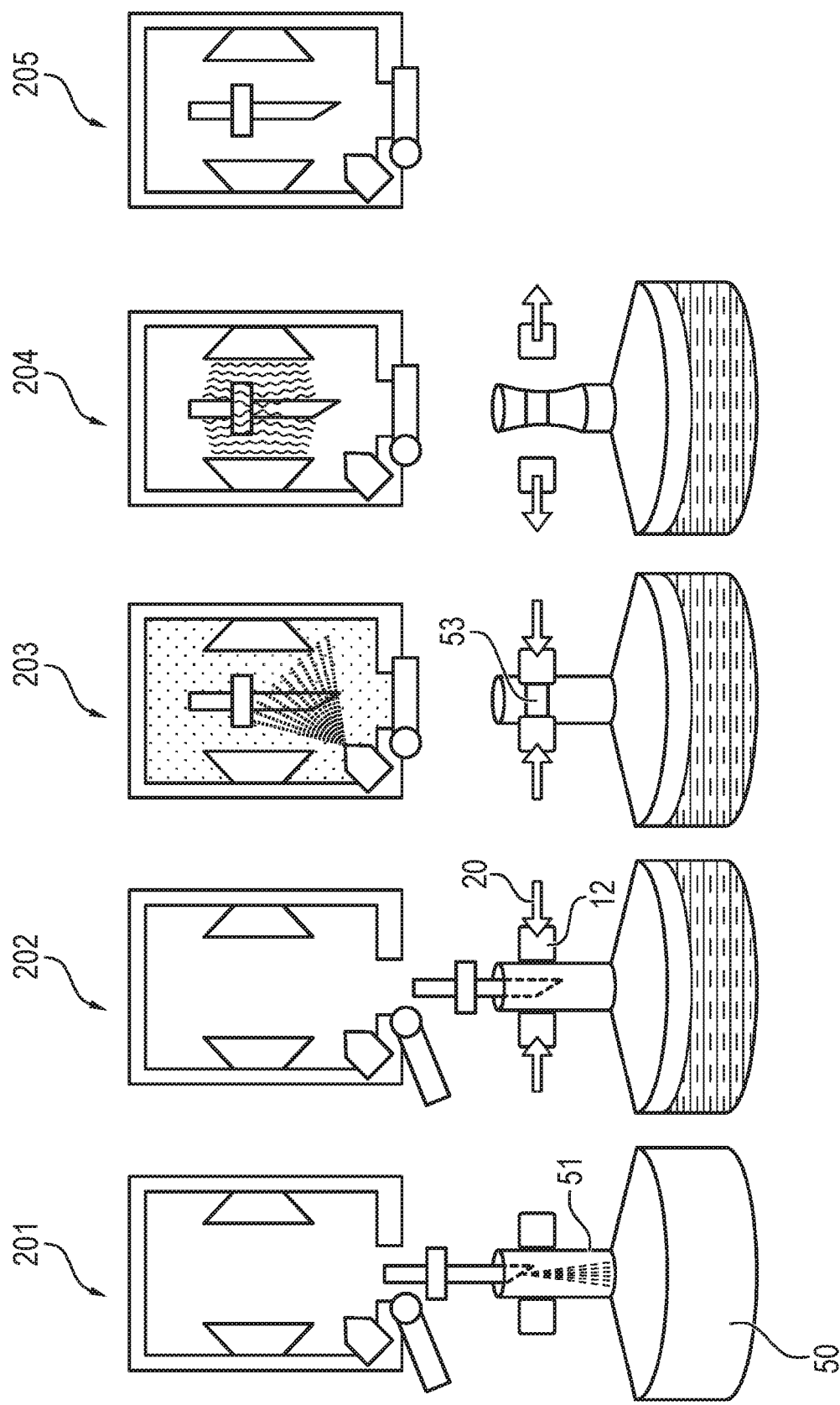

APPARATUS AND METHOD FOR FILLING SOLUTION BAGS FOR DIALYSIS

The invention relates to an apparatus and to a method for filling solution bags for dialysis.

It is in particular customary in the field of peritoneal dialysis to provide the patient with solution bags that are filled with a dialysis solution suitable for the patient. The patient then connects these solution bags to an inflow hose independently or with the aid of trained medical personnel to fill the peritoneum with the solution.

To fill the bags, medical liquid is introduced through a filling tube or through another filling opening of the bag and the filling tube or the opening is then sealed. An apparatus for filling such bags is disclosed in WO 2017/127632 A1.

It is the object of the invention to provide an apparatus for filling solution bags for dialysis by which a sterile filling and a subsequent sealing of the filling tube or of the filling opening can be achieved in a simple manner.

Against this background, the invention relates to an apparatus for filling a solution bag for dialysis with a medical liquid, wherein the apparatus preferably comprises a filling station having a needle for introduction into a filling line or filling opening of the bag, and wherein the needle is a double wall needle having a preferably thermally conducting outer wall and an inner wall, with the outer wall and the inner wall being thermally insulated from one another so that different temperatures can be reliably realized between the outer wall and the inner wall.

The inner wall surrounds the liquid channel of the needle. The outer wall can be heated particularly easily due to the preferably thermally conductive properties of the outer wall, also by a heating element arranged remote from the point to be heated.

The heating element that is directly or indirectly connected to the outer wall is designed such that it can move the temperature of the outer wall, in particular of its outer side, to a value above the temperature of the inner wall.

A heating can be carried out for disinfection, on the one hand, before and after every filling procedure or for a plurality of filling procedures.

The needle can furthermore also be heated before and/or while it is located in the filling line or filling opening. This heating preferably takes place at a temperature at which microbes or pathogens are killed.

A temperature is preferably selected during the heating to melt the plastic material of the solution bag at the inner surface of the filling line or filling opening and to enable a simple pressure sealing of the bag material after removal of the needle. Due to the thermal insulation, a heating of the outer needle wall is not impaired by the liquid located in the liquid channel of the needle and, conversely, the liquid to be introduced into the solution bag is not heated in an unwanted manner, which could possibly result in damage to it.

Provision is made in an embodiment that the outer wall of the needle consists of metal. Metal is not only thermally conductive, but also electrically. Ferromagnetic materials can in particular be suitable. It can be inductively heated or is can be flowed through by electric current for heating. In an embodiment, both the inner wall and the outer wall consist of metal.

The use of plastic for the outer wall and/or inner wall of the needle is generally also covered by the invention.

Provision is made in an embodiment that the thermal insulation is a vacuum insulation. A particularly good thermal insulation effect can be achieved with a vacuum insulation. Alternatively, an insulating gas or air can also be filled between the walls, or an insulation material such as a ceramic material, a plastic material, a fiber material, or foam can be arranged therebetween.

Provision is made in an embodiment that a heating element is arranged at the outer surface of the needle, preferably at a distance from the needle tip. The heating element is arranged such that it emits heat to the thermally conductive outer surface and can thus result in a fast heating of the total outer needle surface up to the tip.

The heating element can, for example, be a ring composed of a ferromagnetic material that can be inductively heated. In this case, the apparatus comprises a coil for generating an alternating magnetic field. The heating element can furthermore be an electrical resistor element that is connected to an electrical contact of the apparatus.

In an embodiment, the apparatus has a UV light source and/or a nozzle for spraying the needle with disinfectant. The UV light source and the nozzle can serve to sterilize the needle before its introduction into the filling line or filling opening of the bag.

In an embodiment, the apparatus has a preparation chamber which can receive the needle. The preparation chamber can comprise a cover to be able to enclose the needle located in the parked position in the chamber. The UV light source or the nozzle for spraying the needle with disinfectant can be arranged within the preparation chamber.

Provision can be made that the apparatus is configured to move the needle in an axial direction between a parked position and a filling position. The linear movement between the parked position and the filling position should be accompanied in the application by an introduction of the needle into the filling line or filling opening and by a drawing of the needle out of the filling line or filling opening. The parked position can be disposed within the optionally present preparation chamber.

Provision is made in an embodiment that the apparatus has clamping jaws that are configured to compress the filling line or filling opening of the bag. The filling line or filling opening can be sealed by means of the clamping jaws if the inner sides of the filling line or filling opening have previously been superficially melted by heating the outer needle wall. Since a melting by the clamping jaws themselves is not required, they can be formed without heating elements.

Provision is made in an embodiment that the apparatus has a plurality of filling stations, preferably of the same construction, with needles, with provision preferably being made that the filling stations are arranged on a carousel rotation station or next to one another in the manner of a conveyor belt.

The plurality of filling stations and needles are preferably all identical.

The filling stations can each comprise a preparation chamber. The throughput can be increased by a use of a plurality of needles. In the case of a carousel rotation station, each filling station can change its rotational position at fixed intervals, with a step in the filling cycle being associated with each rotational position, e.g. fixing the bag at the filling station; introducing the needle into the filling line or filling opening; introducing the liquid; heating the needle and melting the inner surfaces of the filling line or filling opening; withdrawing the needle and clamping the filling line or filling opening for sealing; decoupling the bag; disinfecting the needle in the parked position, etc. Since the needles are always in use in the variant with a suitable interval choice and since bags are always led to and withdrawn from the same position at the filling stations, such an arrangement can be particularly advantageous from a technical production point of view.

This applies accordingly to the use of a conveyor-belt like arrangement of the filling stations.

Against the initially named background, the invention further relates to a method of for filling a solution bag for dialysis with a liquid using an apparatus in accordance with the invention, wherein the needle is introduced into a filling line or filling opening of the solution bag, outputs liquid into the solution bag and is then withdrawn from the filling line or filling opening again. The temperature at the outer side of the outer wall of the needle is higher than at the inner side of the inner wall here.

The liquid output through the liquid channel of the needle can, in dependence on the concept, be a prefabricated dialysis solution, a partial solution, or a solution concentrate and sterile and deionized water.

The filling line or filling opening of the bag can be closed, for example, by a membrane, before the introduction of the needle and the closure can be pierced on the introduction of the needle into the filling line or filling opening. Provision is preferably made for the introduction and withdrawal of the needle that the needle is moved in the axial direction between a parked position and a filling position. A movement of the bag or of the filling line or filling opening is, however, also conceivable and covered by the invention.

Provision is made in an embodiment that the filling process is repeated a multiple of times using the same needle to fill a plurality of solution bags. The needle is therefore used as a reusable needle. The needle can nevertheless be replaceably fastened to the apparatus in order to be able to carry out a replacement after a service life of, for example, some days or several hundred bags.

Provision is made in an embodiment that the outer wall of the needle is heated before the introduction of the needle into the filling line or filling opening, preferably to a temperature of more than 80° C. The heating produces a disinfection of the outer needle surface and of the adjacent bag regions. A heating to a temperature of more than 100° C. is preferred, preferably above 121° C.

The outer needle wall is preferably only briefly maintained at this temperature, for example less than 30 seconds, and preferably less than 10 seconds. Before the introduction of the needle into the filling line or filling opening, it should be cooled again, at least to a temperature below 100° C. and preferably to a temperature below 80° C.

Alternatively or additionally, the outer wall of the needle can be irradiated with UV light and/or sprayed with a disinfectant before the introduction of the needle into the filling line or filling opening.

A heating or another type of disinfecting before a filling process simultaneously corresponds to a heating or another type of disinfecting after a preceding filling process due to the multiple repetition of the filling process. The heating or another type of disinfecting can take place between all filling processes or always after completing a specific number of filling processes, for example after completing two, five, or ten filling processes.

In an embodiment, the needle can be introduced into a preparation chamber for disinfecting between the filling processes, either by withdrawing the needle into the parked position or by imposition of the chamber. The chamber can optionally be closed.

Provision is made in an embodiment that the outer wall of the needle is heated while the needle is introduced in the filling line or filling opening to melt the inner surfaces of the filling line or filling opening by the heat development of the needle and that the filling line or filling opening is compressed after the withdrawal of the needle to seal the filling line or filling opening by connecting its melted inner surfaces.

The needle is here preferably heated to a temperature that results in a superficial softening or melting of the inner surface of the filling line or filling opening. A heating to a temperature of greater than 100° C., greater than 120° C., or greater than 150° C. is preferred.

The filling line or filling opening is typically produced from a thermoplastic. Provision can be made that the thermoplastic of the filling line or filling opening is melted directly or a thermoplastic can be applied for the purpose of welding to the inner surface of the filling line or filling opening, said thermoplastic having a lower melting point. The filling line or filling opening can also already be compressed during the heating and the inner surface of the filling tube or filling opening can thus be pressed onto the heated needle to accelerate the melting.

Provision is made in an embodiment that the outer needle wall is heated inductively or by flowing through of electric current. The heating can here take place directly, that is, by inductive heating of the outer needle wall itself or by a flow of electric current through the outer needle wall itself. Provision can alternatively be made that a heating element in thermal contact with the outer needle wall is heated inductively or by a throughflow of electric current. Examples for the heating element include a metallic ring that is arranged at a spacing from the needle tip at the needle shaft.

Provision is made in an embodiment that a plurality of filling stations of preferably the same construction of the apparatus are simultaneously used, with the same method steps being carried out offset in time or simultaneously at the different filling stations.

Provision can, for example, be made that the first needle is introduced into the first filling line or filling opening of a first bag at a first filling station and the first bag is filled, while the second needle located in a second filling line or filling opening is heated at a second filling station to melt the inner surfaces of the second filling line or filling opening. At a further, third filling station, a third needle can at the same time be drawn from a third filling line or filling opening of a third bag and the third filling line or filling opening can be compressed to seal the third filling line or filling opening by connecting previously melted inner surfaces. The fourth needle can simultaneously be disinfected at a fourth filling station and a fifth needle can cool at a fifth filling station.

The filling stations can be arranged at a rotatable carousel rotation station that is rotated between two method steps by a respective angle that corresponds to a fraction of a whole rotation corresponding to the number of filling stations. An arrangement of a plurality of filling stations next to one another is also conceivable and covered by the invention.

The invention is of particular relevance in connection with decentralized and optionally mobile units for preparing dialysis solutions on site and for direct administration to the patient. It is typically more difficult in such units to ensure the sterility in the filling of the solution bags.

It is pointed out at this point that the terms "a" and "one" do not necessarily refer to exactly one of the elements, even though this represents a possible embodiment, but can also designate a plurality of elements. The use of the plural equally also includes the presence of the element in question in the singular and, conversely, the singular also includes a plurality of the elements in question.

Further details and advantages of the invention result from the embodiments described in the following with reference to the Figures. There are shown in the Figures:

FIG. 1: a schematic representation of a double wall needle of an apparatus in accordance with the invention;

FIG. 2: a schematic representation of a plurality of method steps of a method in accordance with the invention; and FIG. 3: a schematic representation of a plurality of method steps of an alternative variant of a method in accordance with the invention.

A double wall needle 1 for use in an apparatus in accordance with the invention and in a method in accordance with the invention is shown in FIG. 1. It is a double wall needle 1 of stainless steel. A hollow space that is vacuum insulated is provided between the outer wall 2 and the inner wall 4 of the needle 1. The tip 5 of the needle 1 is chamfered to be able to better pierce membranes or other closures in the filling line or filling opening of solution bags.

The needle 1 is a reusable needle that is used in accordance with its intended purpose for the filling of a plurality of solution bags. It is replaceable in a manner not shown in any more detail at the filling station of an apparatus for filling solution bags for dialysis. The liquid channel 6 serves the introduction of liquid into a filling line or filling opening of the bag.

A schematic representation of a plurality of method steps of a variant of a method in accordance with the invention is shown in FIG. 2. The needle 1 shown there is configured as was described in connection with FIG. 1.

In a first method step, the filling step 101, the needle is moved into an extended filling position, with it penetrating into a filling tube not shown in any more detail of a solution bag not shown in any more detail and piercing a membrane. The needle 1 is shown in its filling position in the Figure. Liquid 7 such as a ready-mixed dialysis solution flows from the liquid channel of the needle through the liquid channel of the needle 1 into a filling line or filling opening of the bag.

In a following method step, the withdrawal step 102, the needle 1 is pulled out of the filling line or filling opening of the bag and is moved through an axial movement in translation into a parked position in which the needle 1 is completely received in a preparation chamber 8. The preparation chamber comprises a hatch 9 for closing the chamber 8 at the point at which the needle 1 was withdrawn out of the filling position.

In a further method step, the spray disinfection step 103, the needle 1 within the chamber 8 is sprayed with disinfectant with a closed hatch 9. A nozzle 10 is arranged in the chamber 8 for this purpose.

In a heating and UV disinfection step 104 with a closed hatch 9, the needle 1 within the chamber 8 is then irradiated with UV light. UV light sources 13 are arranged in the chamber for this purpose. At the same time, a coil, not shown in any more detail, arranged next to the chamber 8 has high frequency AC current applied to it to heat a stainless steel ring 11 inductively that is arranged at the shaft of the needle 1 and that is connected in one piece to the outer wall 2. Starting from this ring 11, the outer wall 2 of the total needle is heated to a desired temperature of 120° C. As soon as the desired temperature has been reached, the inductive heating is suspended.

In a last step, the cooling step 105, the needle 1 is stationary within the chamber 8 so that the outer wall 2 can cool to room temperature or to just above room temperature. The method subsequently begins from the start.

A schematic representation of a plurality of method steps of another variant of a method in accordance with the invention is shown in FIG. 3. The needle 1 shown there is in turn configured as was described in connection with FIG. 1.

The filling step 201 of this method corresponds to the filling step 101 of the method shown in FIG. 2.

This step is followed in the method of FIG. 3, however, by a melting step 202 in which the needle 1 is still in its filling position and is received in the filling tube 51, shown this time, of the solution bag 50. In this position, the outer wall 2 of the needle is heated by inductive heating of the ring 11 such as described above in connection with step 104 of FIG. 2. The coil, not shown, that has current applied, is here located outside the chamber 8. A pair of clamping jaws 12 of the apparatus is already pressed from the outside against the filling tube 51 during the heating so that a melting of the inner surface of the filling tube 51 is promoted at the heated outer wall 2 of the needle. The clamping movement of the clamping jaws 12 is symbolized by the arrows 20 in the Figure.

The melting step 202 is followed by a sealing step 203 in which the needle 1 is pulled out of the filling line or filling opening of the bag and, as in step 102 of FIG. 2, is moved by an axial movement in translation into a parked position in which the needle 1 is completely received in a preparation chamber 8. A spray disinfection of the needle takes place there, as in step 103 of FIG. 2. At the same time, the pair of clamping jaws 12 is now fully clamped together to connect the previously melted regions at the inner surface of the filling hose 51 to form a melted seal 52 to thus seal the filling hose 51.

A heating and UV disinfection step 204 and a cooling step 205 follow that in turn correspond to the corresponding steps 104 and 105 of the method in accordance with FIG. 2.

Provision is made that all the steps 101 to 105 or 201 to 205 each take up an identical amount of time. The apparatus in accordance with the invention has five filling stations of the same construction with needles 1 and chambers 8 that are arranged evenly distributed over the periphery of a rotational carousel. The rotational carousel rotates every time after the elapse of a time period that corresponds to the duration of a method step by 72° so that the individual filling stations always take up the position of an adjacent filling station after the completion of a method step before the subsequent method step is initiated. The same method steps are thus always carried out at the same position in the apparatus, with the different filling stations, optionally having different connected bags, always being located at the same specific position of the apparatus on the carrying out of a specific method step.

In a variant, only the needle 1 can change its position by rotation of the carousel and the chamber 8 can be arranged as stationary so that individual elements such as the UV light source and the coil do not have to be designed as redundant.

The invention claimed is:

1. An apparatus for filling a solution bag for dialysis with a medical liquid, wherein the apparatus comprises a needle for introduction into a filling line or filling opening of the bag, characterized in that the needle is a double wall needle having a thermally conductive outer wall and having an inner wall, with a thermal insulation being present between the outer wall and the inner wall; and with a heating element being provided that is configured to heat the outer side of the outer wall to a temperature above the temperature of the inner side of the inner wall, characterized in that the filling line or filling opening consists of a material that can be sealed in a liquid-tight manner by the effect of heat provided by the heated needle.

2. An apparatus in accordance with claim 1, characterized in that the outer all of the needle consists of metal; and/or in that the thermal insulation is a vacuum insulation or an air cushion or gas cushion; and/or in that a heating element is arranged at the outer wall of the needle, at a distance from the needle tip.

3. An apparatus in accordance with claim 1, characterized in that the heating device is an electric heating device.

4. An apparatus in accordance with claim 1, characterized in that the apparatus comprises clamping jaws that are configured to compress the filling line or filling opening of the bag after its filling.

5. An apparatus in accordance with claim 1, characterized in that the apparatus has a filling station that comprises the needle.

6. An apparatus in accordance with claim 1, characterized in that the apparatus has a plurality of identically constructed filling stations having needles, with provision being made that the filling stations are arranged on a carousel rotation station.

7. A method for filling a solution bag for dialysis with a liquid using an apparatus in accordance with claim 1, characterized in that
the needle is introduced into a filling line or filling opening of the solution bag, outputs liquid into the solution bag, and is then withdrawn from the filling line or filling opening again, with the temperature of the outer side of the outer wall of the needle being above the temperature of the inner side of the inner wall of the needle that is in contact with the liquid that flows into the solution bag.

8. A method in accordance with claim 7, characterized in that the method of filling is repeated multiple times using the same needle to fill a plurality of solution bags.

9. A method in accordance with claim 7, characterized in that the outer wall of the needle is heated before and/or during the introduction of the needle into the filling line or filling opening, to a temperature of more than 80° C.

10. A method in accordance with claim 7, characterized in that the outer wall of the needle is heated before or while the needle is introduced in the filling line or filling opening such that the inner surface of the filling line or filling opening is melted by the heat development of the needle; and in that the filling line or filling opening is compressed after the withdrawal of the needle to seal the filling line or filling opening in a liquid-tight manner by connecting its melted inner surfaces.

11. A method in accordance with claim 9, characterized in that the outer needle wall is heated inductively or by throughflow of electric current.

12. A method in accordance with claim 7, characterized in that a plurality of filling stations of the same construction of the apparatus are used simultaneously, with the same method steps being carried out with a time offset or at the same time at different filling stations.

* * * * *